(12) United States Patent
Senkan et al.

(10) Patent No.: US 8,822,372 B2
(45) Date of Patent: Sep. 2, 2014

(54) PROCESS FOR PRODUCING OLEFIN OXIDE (75) Inventors: Selim Senkan, Los Angeles, CA (US); Anusom Seubsai, Los Angeles, CA (US)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/516,226

(22) PCT Filed: Dec. 14, 2010

(86) PCT No.: PCT/US2010/060185
§ 371 (c)(1),
(2), (4) Date: Jul. 26, 2012

(87) PCT Pub. No.: WO2011/075458
PCT Pub. Date: Jun. 23, 2011

(65) Prior Publication Data
US 2012/0283455 A1    Nov. 8, 2012

Related U.S. Application Data (63) Continuation of application No. 12/826,445, filed on Jun. 29, 2010, now abandoned.

(60) Provisional application No. 61/284,324, filed on Dec. 17, 2009.

(51) Int. Cl.
| B01J 27/13 | (2006.01) |
| B01J 23/40 | (2006.01) |
| B01J 23/70 | (2006.01) |
| C07D 301/03 | (2006.01) |
| C07D 301/04 | (2006.01) |
| C07D 301/10 | (2006.01) |
| B01J 23/89 | (2006.01) |
| B01J 35/00 | (2006.01) |
| C07D 301/08 | (2006.01) |
| B01J 37/02 | (2006.01) |
| B01J 35/10 | (2006.01) |
| B01J 21/06 | (2006.01) |

(52) U.S. Cl.
CPC ............ C07D 301/10 (2013.01); C07D 301/04 (2013.01); B01J 23/89 (2013.01); B01J 35/002 (2013.01); C07D 301/08 (2013.01); B01J 37/0201 (2013.01); B01J 35/1019 (2013.01); B01J 21/066 (2013.01); B01J 21/063 (2013.01)
USPC .......................... 502/331; 502/230; 502/326

(58) Field of Classification Search
USPC ........... 502/331, 230, 250, 328; 549/523, 536
See application file for complete search history.

(56) References Cited

U.S. PATENT DOCUMENTS

| 4,497,908 A | 2/1985 | Lewis et al. |
| 6,362,349 B1 | 3/2002 | Kuperman et al. |

(Continued)

FOREIGN PATENT DOCUMENTS

| CN | 1297443 A | 5/2001 |
| CN | 1791586 | 6/2006 |

(Continued)

OTHER PUBLICATIONS

Aldrich, Catalog Handbook of Fine Chemicals, 1998-1999, p. 438,442,1473-1474 (a total of five pages).*

(Continued)

Primary Examiner — T. Victor Oh
(74) Attorney, Agent, or Firm — Foley & Lardner LLP (57) ABSTRACT A process for producing an olefin oxide which comprises reacting an olefin with oxygen in the presence of a catalyst comprising a copper oxide and a ruthenium oxide on a porous support.

13 Claims, 7 Drawing Sheets

(56) References Cited

U.S. PATENT DOCUMENTS

| | | | |
|---|---|---|---|
| 6,401,840 | B1 | 6/2002 | Hay et al. |
| 6,403,840 | B1 | 6/2002 | Zhou et al. |
| 6,765,101 | B1 | 7/2004 | Bhasin et al. |
| 7,348,444 | B2 | 3/2008 | Evans et al. |
| 2003/0187283 | A1 | 10/2003 | Jansen et al. |
| 2003/0191328 | A1 | 10/2003 | Jansen et al. |

FOREIGN PATENT DOCUMENTS

| | | |
|---|---|---|
| JP | 2002-371074 A | 12/2002 |
| JP | 2004-531542 | 10/2004 |
| WO | WO02/088102 A1 | 11/2002 |
| WO | WO2011/075458 A1 | 6/2011 |
| WO | WO-2011/075459 A1 | 6/2011 |

OTHER PUBLICATIONS

U.S. Office Action for U.S. Appl. No. 13/516,222 dated Sep. 27, 2013.
Communication (Supplementary European Search Report) in EP Appln No. 10838192.2 dated Jan. 14, 2014.
First Office Action in CN Appln No. 201080057749 dated Nov. 15, 2013.
Lu, J. et al. "Epoxidation of propylene on NaCl-modified silver catalysts with", Applied Catalysis A: General, 2002, vol. 237, pp. 11-19.
Seubsai, A. et al. "New Catalytic Materials for the Direct Epoxidation of Propylene by Molecular Oxygen", Chemcatchem, 2010, vol. 3, pp. 174-179.
Office Action dated Feb. 12, 2014 received in Japanese Patent Application No. 2012-532152.
Office Action dated Feb. 12, 2014 received in Japanese Patent Application No. 2012-532151.
Office Action for U.S. Appl. No. 13/516,222 dated Jan. 17, 2014.
Office Action issued in counterpart Japanese Patent Application No. 2012-532151 dated Nov. 12, 2013, with English translation.
Office Action issued in counterpart Japanese Patent Application No. 2012-532152 dated Nov. 12, 2013, with English translation.
Extended European Search Report issued in related European Application No. 10638193.0 dated Oct. 21, 2013.
Chinese Office Action received in Chinese Patent Application No. 201080057846.9 dated Feb. 20, 2014.
Kahlich, D., et al., "Propylene Oxide," Ullmann's Encyclopedia of Industrial Chem., (2006), John Wiley & Sons, Inc., pp. 1-25.
Nijhuis, T.A., et al., "The Production of Propene Oxide: Catalytic Processes and Recent Developments," Ind. Eng. Chem. Res., (2006), pp. 3447-3459, vol. 45.
Van Santen, R.A., et al., "The Mechanism of Ethylene Epoxidation," Journal of Catalysis, (1986), pp. 530-539, vol. 98.
Carter, E.A., et al., "The Surface Atomic Oxyradical Mechanism for Ag-Catalyzed Olefin Epoxidation," Journal of Catalysis, (1988), pp. 80-82, vol. 112.
Hayashi, T., et al., "Selective Vapor-Phase Epoxidation of Propylene over Au/$TiO_2$ Catalysts in the Presence of Oxygen and Hydrogen," Journal of Catalysis, (1998), pp. 566-575, vol. 178.
Sivadinarayana, C., et al., "The Nature of the Surface Species Formed on Au/$TiO_2$ during the Reaction of $H_2$ and $O_2$: An Inelastic Neutron Scattering Study," J. Am. Chem. Soc., (2004), pp. 38-39, vol. 126.
Lambert, R.M. et al., "Heterogeneous alkene epoxidation: past, present and future", Journal of Molecular Catalysis A: Chemical, (2005), pp. 27-33, vol. 228.
Vaughan, O.P.H., et al., "Copper as a selective catalyst for the epoxidation of propene," Journal of Catalysis, (2005), pp. 401-303, vol. 236.
Zhu, W, et al., "Cu(I)-Catalyzed Epoxidation of Propylene by Molecular Oxygen," J. Phys. Chem. C, (2008), pp. 7731-7734, vol. 112.
Song, Z, et al., "Gas-phase epoxidation of propylene through radicals generated by silica-supported molybdenum oxide," Applied Catalysis A: General, (2007), pp. 142-141, vol. 316.

Song, Z, et al., "Surface-Initiated Gas-Phasr Epoxidation of Propylene with Molecular Oxygen by Silica-Supported Molybdenum Oxide: Effects of Addition of $C_3H_8$ or NO and Reactor Design," Catal Lett, (2008), pp. 33-38, vol. 121.
Zhang, Q., et al., "Iron-catalyzed propylene epoxidation by nitrous oxide: Toward understanding the nature of active iron sites with modified Fe-MFI and Fe-MCM-41 catalysts," Journal of Catalysis, (2006), pp. 105-116, vol. 239.
Wang, X., et al., "Iron-Catalyzed Propylene Epoxidation By Nitrous Oxide: Studies on the Effects of Alkali Metal Salts," J. Phys. Chem. B, (2005), pp. 23500-23508, vol. 109.
Alexeev, O.S. et al., "Supported Bimetallic Cluster Catalysts," Ind. Eng. Chem. Res., (2003), pp. 1571-1587, vol. 42.
Lu, J., et al., "Epoxidation of Propylene on NaCl-Modified $VCe_{1-x}CU_x$ Oxide Catalysts with Direct Molecular Oxygen as the Oxidant," Journal of Catalysis, (2002), pp. 552-555, vol. 211.
Takahashi, A., et al., "Effects of added 3d transition-metals on Ag-based catalysts for direct epoxidation of propylene by oxygen," Applied Catalysis A: General, (2005), pp. 34-39, vol. 294.
Sacaliuc, E., et al.; "Propene epoxidation over Au/Ti-SBA-15 catalysts," Journal of Catalysis, (2007), pp. 235-248, vol. 248.
Sinha, A.K., et al., "Vapor phase propylene epoxidation over Au/Ti-MCM-41 catalysts prepared by different Ti incorporation modes," Applied Catalysis A: General, (2003), pp. 243-252, vol. 240.
Kahn, M., et al., "High Throughput Synthesis and Screening of New Catalytic Materials for the Direct Epoxidation of Propylene," Combinatorial Chemistry & High Throughput Screening, (2010), pp. 67-74, vol. 13.
Senkan, S., et al., "High-Throughput Testing of Heterogeneous Catalyst Libraries Using Array Microreactors and Mass Spectrometry," Angew. Chem. Int. Ed., (1999), pp. 2794-2799, vol. 38, No. 18.
Senkan, S. Selim., et al., "Discovery and Optimization of Heterogeneous Catalysts by Uisng Combinatorial Chemistry," Angew. Chem. Int. Ed., (1999), pp. 791-795, vol. 38, No. 6.
Senkan, S., "Combinatorial Heterogeneous Catalysis—A New Path in an Old Field," Angew. Chem. Int. Ed., (2001), pp. 312-329, vol. 40.
Senkan, S., et al., "High-throughput metal nanoparticle catalysis by pulsed laser ablation," Catalysis Today, (2006), pp. 291-296, vol. 117.
Duan, S., et al., Catalytic Oonversion of Ethanol to Hydrogen Using Combinatorial Methods, Ind. Eng. Chem. Res., (2005), pp. 6361-6386, vol. 44.
Sinfelt, J.H., "Bimetallic Systerns of Immiscible Components," Supplied by The British Library—"The world's knowledge," pp. 33-50, Abstract, p. 62, Chapter 3, 1994.
Jankowiak, J.T., et al., "Ethylene epoxidation over silver and copper—silver bimetallic catalysts: I. Kinetics and selectivity," Journal of Catalysis: (2005), pp. 386-378, vol. 236.
Schoenmaker-Stolk, M.D., et al., "The Catalytic Hydrogenation of Benzene Over Supported Metal Catalysts. III. Gas-Phase Hydrogenation of Benzene Over Silica-Supported Ru—Cu Catalysts," Applied Catalysis, (1987), pp. 339-352, vol. 30.
Matar S. et al., "Chemicals Based on Propylene," Chem. of Petrochemical Processes, Gulf Pub. Co., Houston, 1994, Supplied by The British Library—"The world's knowledge," pp. 207-232, Chapter 8.
Trent, D.L., "Propylene Oxide," Propylene Oxide, 1996, pp. 271-302, vol. 20.
Canning, Kathie, "DOW. BASF Join Forces in PO Production," In The News, Supplied by The British Library—"The world's knowledge.", 2002.
Monnier, John, "The direct epoxidation of higher olefins using molecular oxygen," Applied Catalysis A: General, (2001), pp, 73-91, vol. 221.
Huang, J., et al., "Propene Epoxidation with Dioxygen Catalyzed by Gold Clusters.", Angew. Chem. Int. Ed., (2009), pp. 7862-7866, vol. 48.
Hayashi, T., et al., "Formation of Propylene Oxide by the Gas-Phase Reaction of Propane and Propene Mixture with Oxygen," Ind. Eng. Chem. Res., (1995), pp. 2298-2304, vol. 34.
Hayashi, T., et al., "Selective Vapor-Phase Epoxidation of Propyiene over Au/$TiO_2$ Catalysts in the Presence of Oxygen and Hydrogen," Journal of Catalysis (1998), pp. 566-575, vol. 178.

(56) References Cited

OTHER PUBLICATIONS

Uphade, B.S., et al., "Effect of physical mixing of CsCl with Au/Ti-MCM-41 on the gas-phase epoxidation of propene using $H_2$ and $O_2$: Drastic depression of $H_2$ consumption," Applied Catalysis A: General, (2000): pp. 43-50, vol. 190.

Sinha, A.K., et al., "A Three-Dimensional Mesoporous Titanosilicate Support for Gold Nanoparticles: Vapor-Phase Epoxidation of Propene with High Conversion," Angew. Chem. Int. Ed., (2004), pp. 1546-1548, vol. 43.

Murata, K., et al., "Oxidation of propene by molecular oxygen over Ti-modified silicate catalysts," Chem. Commun., (2001), pp. 1356-1357.

Murata, K., et al., "Direct vapor phase oxidation of propylene by molecular oxygen over MCM-41 or MCM-22 based catalysts," Catalysis Communications, (2003), pp. 385-391, vol. 4.

Nijhuis, T.A., et al., "The direot epoxidation of propene by molten salts," Applied Catalysis A: General, (2000), pp. 217-224, vol. 196.

Haruta, M. et al., "Advances in the catalysis of Au nanoparticles," Applied Catalysis A: General, (2001), pp. 427-437, vol. 222.

Senkan, Selim, et al., "Discovery and Optimization of Heterogeneous Catalysts by Using Combinatorial Ohemistry"; Angew. Chem. Int. Ed., (1999), pp, 791-795. vol. 38, No. 6.

Torres, D., et al., "Low Basicity Oxygen Atoms: A Key in the Search for Propylene Epoxidation Catalysts," Angew. Chem. Int. Ed., (2007), Inkerscience, Jhon Wiley, New York, 1963, pp. 2055-2058, vol. 46.

Wyckoff, R.W.G., "Octahedrally Coordinated Compounds," Crystal Structures, Interscience, John Wiley, New York, 1963, pp. 250-253, Chapter IV.

Onal, I., et al., "Propylerie Epoxidation: High-Throughput Screening of Supported Metal Catalysts Combinatorially Prepared by Rapid Sol-Gel Method," Top Catal, (2010), pp. 92-99, vol. 53.

Kahn, M., et al., "New Catalytic Materials for the Direct Epoxidation of Propylene by Oxygen: Application of High-Throughput Pulsed Laser Ablation," Top Catal, (2010), pp. 86-91, vol. 53.

International Search Report cited in related International Patent Application No. PCT/US2010/060185, completed Jan. 27, 2011.

Written Opinion of the International Searching Authority cited in related International Patent Application No. PCT/US2010/060185, completed Jan. 27, 2011.

Chinese Second Office Action dated Jun. 10, 2014 issued in Application No. 201080057749.X.

Office Action in European Patent Application No. 10838192.2 dated Jul. 1, 2014.

\* cited by examiner

PROCESS FOR PRODUCING OLEFIN OXIDE

CROSS-REFERENCE TO RELATED APPLICATION(S)

This application is the National Phase of International Patent Application No. PCT/US2010/060185, filed Dec. 14, 2010, published as WO 2011/075458, which claims priority to U.S. Provisional Patent Application No. 61/284,324, filed Dec. 17, 2009. This application is also a continuation of U.S. patent application Ser. No. 12/826,445, filed Jun. 29, 2010. The contents of these applications are herein incorporated by reference in their entirety.

FIELD OF THE INVENTION

The present invention relates to a process for producing an olefin oxide.

BACKGROUND ART

Olefin oxides, as for example propylene oxide, are amongst the most important chemicals widely used for the preparation of various textiles and plastics. Several studies have intensively attempted to search for a process to obtain an olefin oxide with a high production rate hoping for an economically feasible plant design.

Recently, copper-modified catalysts have become attractive for propylene epoxidation [J. Catal. 236 (2005) 401]. A study of a single crystal of metallic copper showed that $Cu^0$ was intrinsically a much more selective epoxidation catalyst for alkenes containing allylic hydrogen than $Ag^0$ [J. Mol. Catal. A 228 (2005) 27]. It has been found that $Cu^I$ supported on a silica ($SiO_2$) catalyst was also efficient for the epoxidation under oxygen-rich conditions [J. Phys. Chem. C 112 (2008) 7731].

Furthermore, a few lead single-metal modified catalysts have been examined for the direct gas phase epoxidation of propylene such as molybdenum on $SiO_2$ [Appl. Catal. A 316 (2007) 142.; Catal. Lett. 121 (2008) 33] and iron on Mobil Composition of Matter (MCM)-41 [J. Catal. 239 (2006) 105; JJ. Phys. Chem. B 109 (2005) 23500].

Supported multimetallic catalysts for propylene epoxidation have attracted great interest since they often present excellent catalytic properties in comparison to individual metal components [Ind. Eng. Chem. Res. 42 (2003) 1571].

There are some proposed catalysts such as sodium chloride-modified $VCe_xCu_{1-x}$ mixed oxide [J. Catal. 211 (2002) 552], silver-based catalysts containing nickel metal [Appl. Catal. A 294 (2005) 34], gold on titanium-SBA-15 [J. Catal. 248 (2007) 235], and gold on MCM-41 [Appl. Catal. A 240 (2003) 243].

SUMMARY OF THE INVENTION

The present invention provides:
[1] A process for producing an olefin oxide which comprises reacting an olefin with oxygen in the presence of a catalyst comprising a copper oxide and a ruthenium oxide on a porous support.
[2] The process according to [1], wherein the porous support comprises $Al_2O_3$, $SiO_2$, $TiO_2$ or $ZrO_2$.
[3] The process according to [1], wherein the porous support comprises $SiO_2$.
[4] The process according to any one of [1] to [3], wherein the total amount of the copper oxide and the ruthenium oxide in the catalyst is 0.01 to 80% by weight of the amount of the catalyst.
[5] The process according to any one of [1] to [4], wherein the copper/ruthenium metal weight ratio in the catalyst is 1/99 to 99/1.
[6] The process according to any one of [1] to [5], wherein the copper oxide is CuO.
[7] The process according to any one of [1] to [6], wherein the ruthenium oxide is $RuO_2$.
[8] The process according to any one of [1] to [7], wherein the olefin is propylene and the olefin oxide is propylene oxide.
[9] The process according to any one of [1] to [8], wherein the catalyst is obtained by impregnating a porous support with a solution containing copper and ruthenium ions to prepare a composition, followed by calcining the composition.
[10] The process according to any one of [1] to [9], which comprises reacting an olefin with oxygen at a temperature of 100 to 350° C.
[11] A catalyst for producing an olefin oxide which comprises a copper oxide and a ruthenium oxide on a porous support.
[12] The catalyst according to [11] which is obtained by impregnating a porous support with a solution containing copper and ruthenium ions to prepare a composition, followed by calcining the composition.
[13] The catalyst according to [11] or [12], wherein the porous support comprises $Al_2O_3$, $SiO_2$, $TiO_2$ or $ZrO_2$.
[14] The catalyst according to [11] or [12], wherein the porous support comprises $SiO_2$.
[15] The catalyst according to any one of [11] to [14], wherein the olefin oxide is propylene oxide.
[16] Use of a catalyst for producing an olefin oxide, said catalyst comprising a copper oxide and a ruthenium oxide on a porous support.
[17] The use of a catalyst according to [16], wherein the olefin oxide is propylene oxide.

DETAILED DESCRIPTION OF THE INVENTION

The process of the present invention comprises reacting an olefin with oxygen in the presence of a catalyst comprising a copper oxide and a ruthenium oxide.

In the catalyst, the copper oxide and the ruthenium oxide are supported on a porous support. This catalyst is valuable for producing an olefin oxide, which is one aspect of the present invention.

The porous support has pores capable of supporting the copper oxide and the ruthenium oxide. The porous support comprises preferably $Al_2O_3$, $SiO_2$, $TiO_2$ or $ZrO_2$, more preferably $TiO_2$ or $SiO_2$, still more preferably $SiO_2$. Examples of the porous support comprising $SiO_2$ include mesoporous silica. Such a porous support may also comprise zeolites.

If the catalyst comprises $SiO_2$ as a support, olefin oxides can be prepared with good yield and good selectivity.

The catalyst may comprise one or more kinds of the copper oxide.

The copper oxide is usually composed of copper and oxygen. Examples of the copper oxide include $Cu_2O$ and $CuO$. The copper oxide is preferably $CuO$.

The catalyst may comprise one or more kinds of the ruthenium oxide. The ruthenium oxide is usually composed of ruthenium and oxygen.

Examples of the ruthenium oxide include $RuO_4$, and $RuO_2$. The ruthenium oxide is preferably $RuO_2$. The catalyst preferably comprises $CuO$ and $RuO_2$, because such metal oxides can contribute to improved olefin oxide selectivity.

In the catalyst, the total content of the copper oxide and the ruthenium oxide is preferably 0.01 to 80% by weight of the amount of the catalyst. When the total content falls within such range, the olefin oxide yield and selectivity can be further improved. The lower limit of the total content is more preferably 0.05% by weight, still more preferably 0.1% by weight of the amount of the catalyst. The upper limit of the total content is more preferably 50% by weight, and still more preferably 30% by weight of the amount of the catalyst.

The copper/ruthenium metal weight ratio in the catalyst is 1/99 to 99/1. When the metal weight ratio falls within such a range, the olefin oxide selectivity can be further improved.

The lower limit of the metal weight ratio is more preferably 2/98, still more preferably 3/97. The upper limit of the metal weight ratio is more preferably 98/2, still more preferably 97/3.

Production of the catalyst is not restricted to a specific process.

For example, the catalyst is obtained by impregnating a porous support with a solution containing copper and ruthenium ions to prepare a composition, followed by calcining the composition. The support can be in form of powder, or shaped to a desired structure as necessary.

The solution containing copper and ruthenium ions can be prepared by dissolving a copper metal salt and a ruthenium metal salt in a solvent. Examples of the copper metal salt include copper acetate, copper ammonium chloride, copper bromide, copper carbonate, copper ethoxide, copper hydroxide, copper iodide, copper isobutyrate, copper isopropoxide, copper oxalate, copper oxychloride, copper nitrates, and copper chlorides. Examples of the ruthenium metal salt include, for example, a halide such as ruthenium bromide, ruthenium chloride, ruthenium iodide, an oxyhalide such as $Ru_2OCl_4$, $Ru_2OCl_5$ and $Ru_2OCl_6$, a halogeno complex such as $[RuCl_2(H_2O)_4]Cl$, an ammine complex such as $[Ru(NH_3)_5H_2O]Cl_2$, $[Ru(NH_3)_5Cl]Cl_2$, $[Ru(NH_3)_6]Cl_2$ and $[Ru(NH_3)_6]Cl_3$, a carbonyl complex such as $Ru(CO)_5$ and $Ru_3(CO)_{12}$, a carboxylate complex such as $[Ru_3O(OCOCH_3)_6(H_2O)_3]$ ruthenium nitrosylchloride and $[Ru_2(OCOR)_4]Cl$ (R=alkyl group having 1 to 3 carbon atoms), a nitrosyl complex such as $[Ru(NH_3)_5(NO)]Cl_3$, $[Ru(OH)(NH_3)_4(NO)](NO_3)_2$ and $[Ru(NO)](NO_3)_3$, an amine complex, an acetylacetonate complex, and ammonium salt such as $(NH_4)_2[RuCl_6]$. If any of copper metal salts and ruthenium metal salts contains a halogen ion, the halogen ion may be presented in the obtained catalyst. Such halogen ion presented in the catalyst may form salts or compounds with copper or ruthenium.

The solution may contain acidic or basic compounds in order to control its pH.

Examples of the solvent for the solution include water, alcohols such as methanol or ethanol, and ethers.

The total amount of the porous support is not limited to a specific range, preferably 20 to 99.99% by weight, more preferably 50 to 99.95% by weight, and more preferably 70 to 99.9% by weight of the amount of the catalyst.

The composition as prepared is preferably dried at a temperature of approximately 40 to approximately 200° C. before calcining it. Drying may be performed under an atmosphere of air or also under an inert gas atmosphere (for example Ar, $N_2$, He) at standard pressure or reduced pressure. The drying time is preferably in the range from 0.5 to 24 hours. After drying, the composition can be shaped to a desired structure as necessary.

Calcining the composition is not limited, but it is preferably performed under a gas atmosphere containing oxygen. Examples of such a gas include air and oxygen. The gas may be used after being mixed at an appropriate ratio with a diluting gas such as nitrogen, helium, argon, and water vapor. An optimal temperature for calcination varies depending on the gas, the composition or the like, however, a too high temperature may cause agglomeration of the ruthenium oxide and the copper oxide.

Accordingly, the calcination temperature is typically 200 to 800° C., preferably 400 to 600° C.

The catalyst can be used as powder, but it is usual to shape desired structures such as spheres, pellets, cylinders, rings or hollow cylinders, stars. The catalyst can be shaped by a known procedure such as extrusion, ram extrusion, tableting. The calcination is normally performed after shaping desired structures, but it can also be performed before shaping them.

Next, the following explains the reaction of an olefin with oxygen in the presence of the catalyst as described above.

In the present invention, olefins may have a linear or branched structure and contain usually 2 to 10, preferably 2 to 8 carbon atoms. Examples of olefins include preferably ethylene, propylene, butene, pentene, hexene, heptene and octene, more preferably ethylene, propylene and butene, and still more preferably propylene.

The reaction is generally performed in the gas phase. In the reaction, an olefin and oxygen may be fed respectively in the form of a gas. An olefin and oxygen may also be fed in the form of their mixed gas. Olefin and oxygen gases may be fed with diluent gases. Examples of the diluent gases include nitrogen or rare gases, such as argon and helium.

As oxygen source, pure oxygen may be used, or a mixed gas containing a gas inactive to the reaction, such as air, may be used. The amount of oxygen used varies depending on the reaction type, the catalyst, the reaction temperature or the like. The amount of oxygen is typically 0.01 to 100 mol, and preferably 0.03 to 30 mol, and more preferably 0.25 to 10 mol, with respect to 1 mol of an olefin.

The reaction is performed at a temperature generally of 100 to 350° C., preferably of 120 to 330° C., more preferably of 170 to 310° C.

The present reaction is carried out under reduced pressure to increased pressure. By carrying out the reaction under such a pressure, the productivity and selectivity of olefin oxide can be improved. Reduced pressure means a pressure lower than an atmospheric pressure. Increased pressure means a pressure higher than atmospheric pressure. Under reduced pressure to increased pressure, the pressure is typically in the range of 0.01 to 3 MPa, and preferably in the range of 0.02 to 2 MPa, in the absolute pressure.

The reaction may be carried out as a batch reaction or a continuous reaction, preferably as a continuous reaction for industrial application. The reaction of the present invention may be carried out by mixing an olefin and oxygen and then contacting the mixture with the catalyst under reduced pressure to the increased pressure.

The reactor type is not limited. Examples of reactor types are fluid bed reactor, fixed bed reactor, moving bed reactor, and the like, preferably fixed bed reactor. In the case of using fixed bed reactor, single tube reactor or multi tube reactor can be employed. More than one reactor can be used. If the number of reactors is large, small reactors as for example microreactors, can be used, which can have multiple channels. Adiabatic type or heat exchange type may also be used.

In the present invention, the olefin oxide may have a linear or branched structure and contains usually 2 to 10, preferably 2 to 8 carbon atoms. Examples of the olefin oxide include preferably ethylene oxide, propylene oxide, butene oxide, pentene oxide, hexene oxide, heptene oxide and octene oxide, more preferably ethylene oxide, propylene oxide and butene oxide, and still more preferably propylene oxide.

The olefin oxide as obtained can be collected by a method known in the art such as separation by distillation.

EXAMPLES

In Examples, each measurement was performed according to the following method.
1. Data analysis was conducted by an on-line Micro-Gas Chromatograph (Varian, CP-4900) equipped with a thermal conductivity detector (TCD), PoraPLOT U (10M) and Molecular sieve 13X (10M).
2. The detected products were propylene oxide (PO), acetone (AT), acetaldehyde (AD), $CO_x$ ($CO_2$ and CO), and propanal+acrolein (PaL+AC).

Note: PaL+AC are reported together since the two compounds appear at the same retention time, although the PaL is typically only found in trace amounts.

The products were analyzed by gas chromatography (GC). GC calibrations for propylene, oxygen, and $CO_2$ were performed using mass flow controllers (MKS) and He as a carrier gas.

Calibrations for PO, AC, AT and AD were performed by vaporizing known quantities of a liquid in a heated, evacuated 2250 cm³ stainless steel tank and using He as a carrier gas. All calibrations yielded linear 5-point curves with $R^2$ of at least 0.995, using the peak area as the basis for GC calculations. Contents of each product were determined based on two different calibrations prepared by the method as mentioned above. Hereinafter, the analysis based on one of the calibrations is referred as to "analysis (1)", and the analysis based on the other calibration is referred as to "analysis (2)".

3. The propylene conversion, product selectivity, and yield (calculated as selectivity of product×propylene conversion) of the products were calculated based on the carbon balance. Propylene conversions ($X_{PR}$) were calculated according to the following expression:

$$X_{PR} = \{[PO+AC+AT+2AD/3+CO_2/3]_{out}/[C_3H_6]_{in}\} \times 100\%;$$

and PO selectivities ($S_{PO}$) were then calculated using the following expression:

$$S_{PO} = \{[PO]/[PO+AC+AT+2AD/3+CO_2/3]\} \times 100\%$$

Example 1

Aqueous solutions of Ru [$(NH_4)_2RuCl_6$, Aldrich] and Cu [$Cu(NO_3)_2$, Alfa Aesar, ACS, 98.0%-102.0%] were mixed at a metal weight ratio of 1:1, to prepare a metal salt solution. The metal salt solution was introduced into a $SiO_2$ support powder (surface area 325 m²/g) and left to penetrate the support for 24 hours in the air. The resulting material was collected from the solution, dried at 120° C. for 8 hours and calcined at 500° C. for 6 hours in the air to give a catalyst with a Cu/Ru metal weight ratio of 1/1 at the total metal loading of 5 wt %.

The catalyst (5.0 mg) was placed in a well of a reactor as mentioned in Angew. Chem. Int. Ed. 38 (1999) 2794, equipped with array microreactors, wells along each reactor channel and a passivated 200 micron ID capillary sampling probe within the reactor channel. The mixture gas consisting of 14 vol % propylene ($C_3H_6$), 26 vol % $O_2$, and 60 vol % He was fed to the well at a gas hourly space velocity (GSHV) of 20,000 h$^{-1}$ with a mass flow controller (MKS, Andover, Mass.), at a reactor temperature of 250° C. Gas sampling was accomplished by withdrawing reactor exit gases using the passivated 200 micron ID capillary sampling probe.

The result of the production was determined based on each caribration as mentioned above, which is shown as follow. Propylene oxide selectivity: 14.8%, propylene oxide yield: 0.16%, and propylene conversion: 1.1% (analysis (1)) Propylene oxide selectivity: 10.5%, propylene oxide yield: 0.16%, and propylene conversion: 1.5% (analysis (2))

Example 2

Fifteen (15) catalysts were prepared in the same manner as Example 1, except that the metal contents were X wt % Cu, (5-X) wt % Ru, where 0≤X≤5. Production of propylene oxide was carried out in the same manner as described in Example 1.

Figure 1:
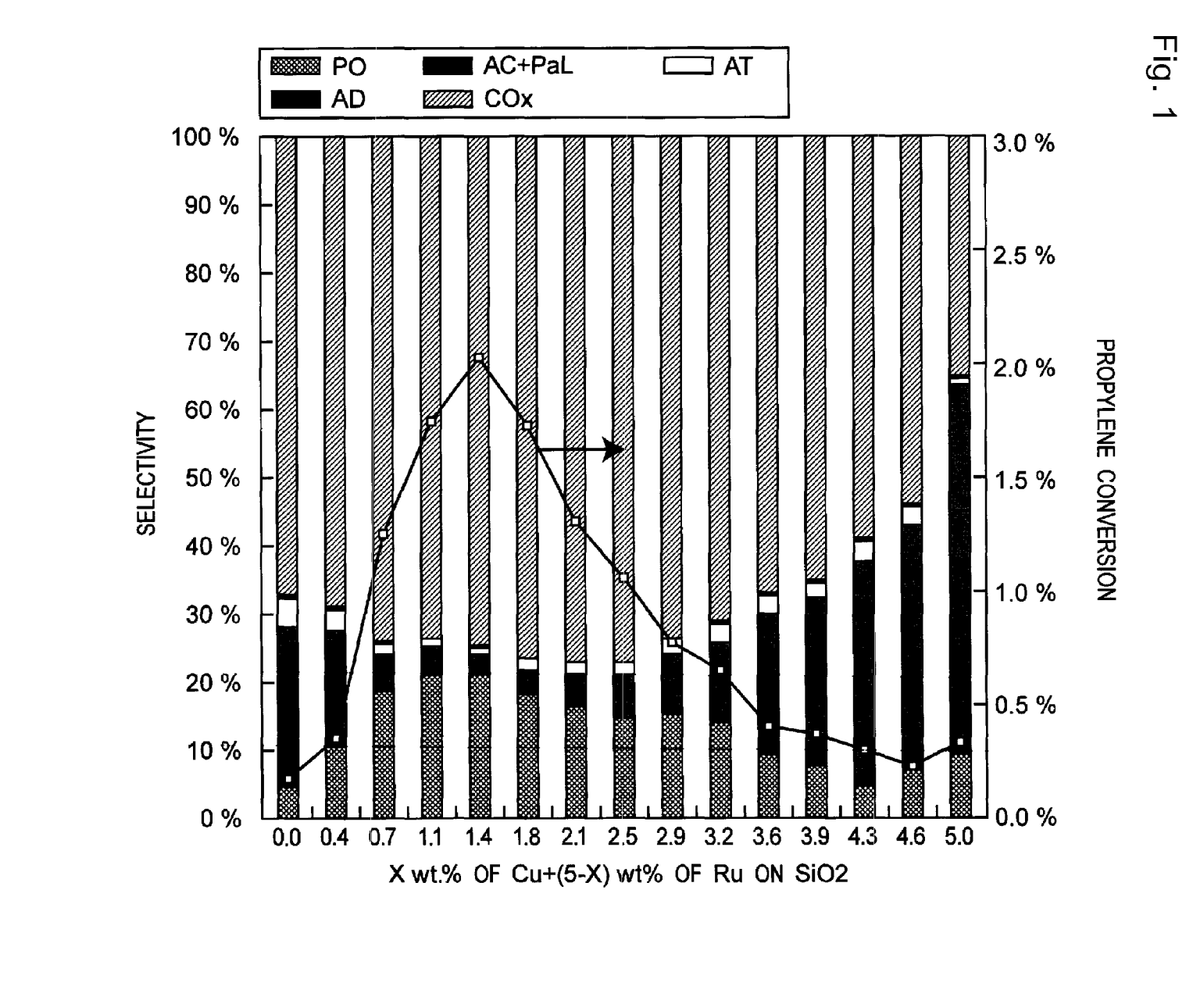
FIG. 1 is a graph showing the result of Example 2, analysis (1).
Figure 2:
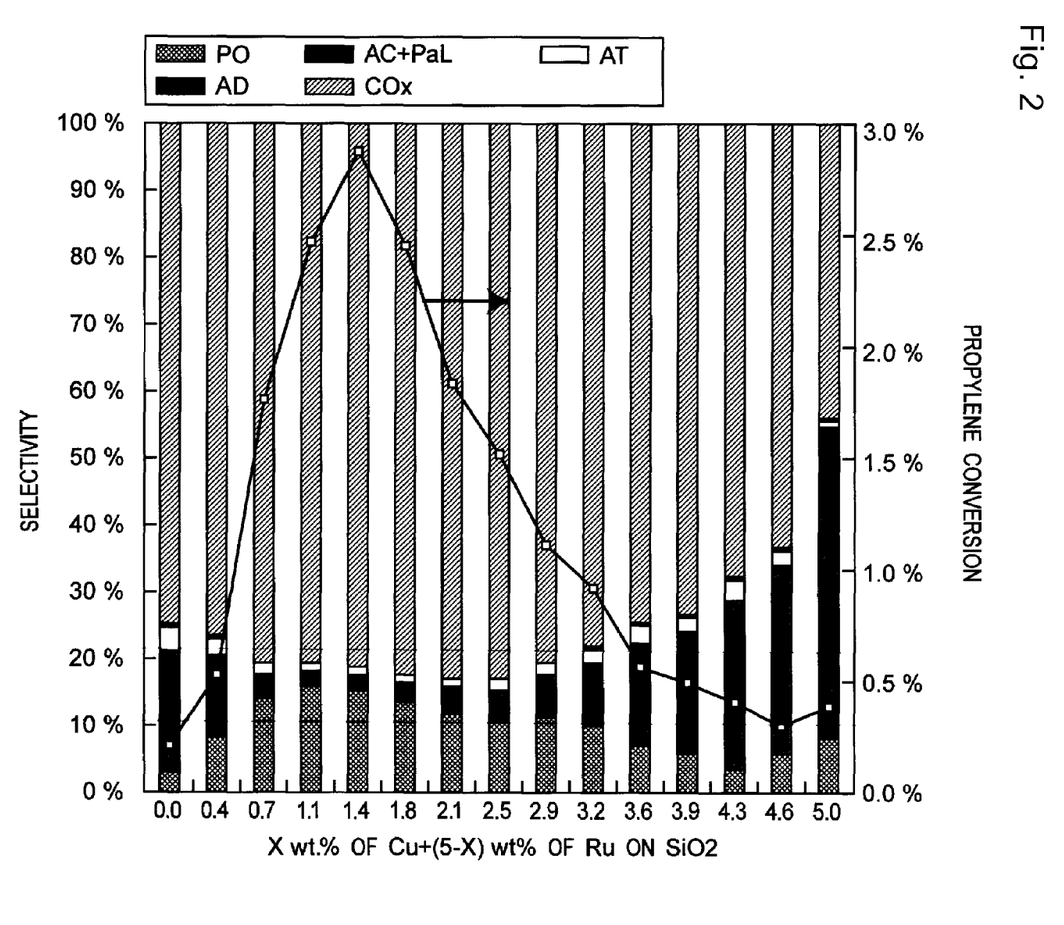
FIG. 2 is a graph showing the result of Example 2, analysis (2).

The result based on the analysis (1) is shown in FIG. 1. The result based on the analysis (2) is shown in FIG. 2.

Example 3

Five (5) catalysts were prepared in the same manner as Example 1, except that the total metal amount in each catalyst was 1.25, 2.5, 7.5, 10 or 15 wt % with the metal weight ratio of Ru/Cu=3.6/1.4.

Production of propylene oxide was carried out in the same manner as Example 1, except that each of the catalysts as obtained was used.

Figure 3:
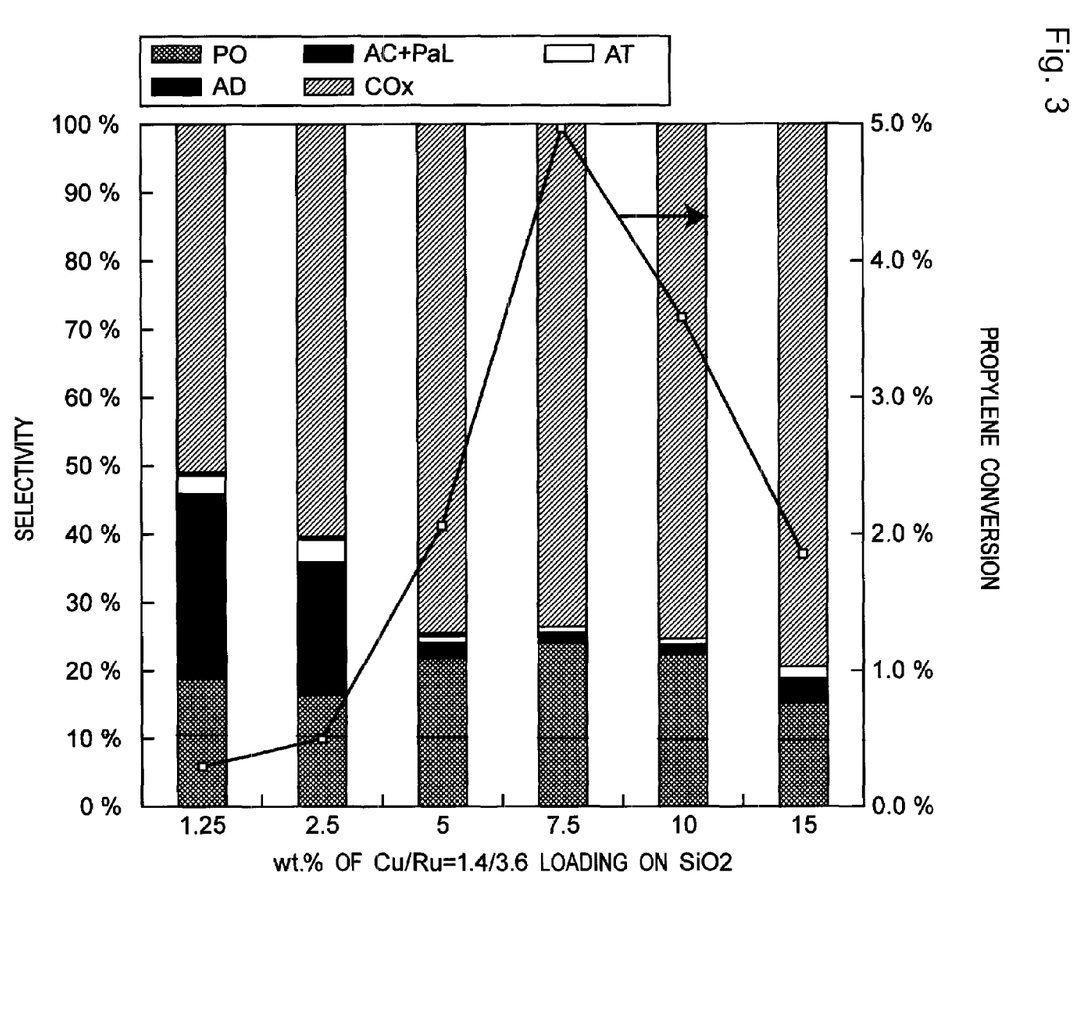
FIG. 3 is a graph showing the result of Example 3, analysis (1).
Figure 4:
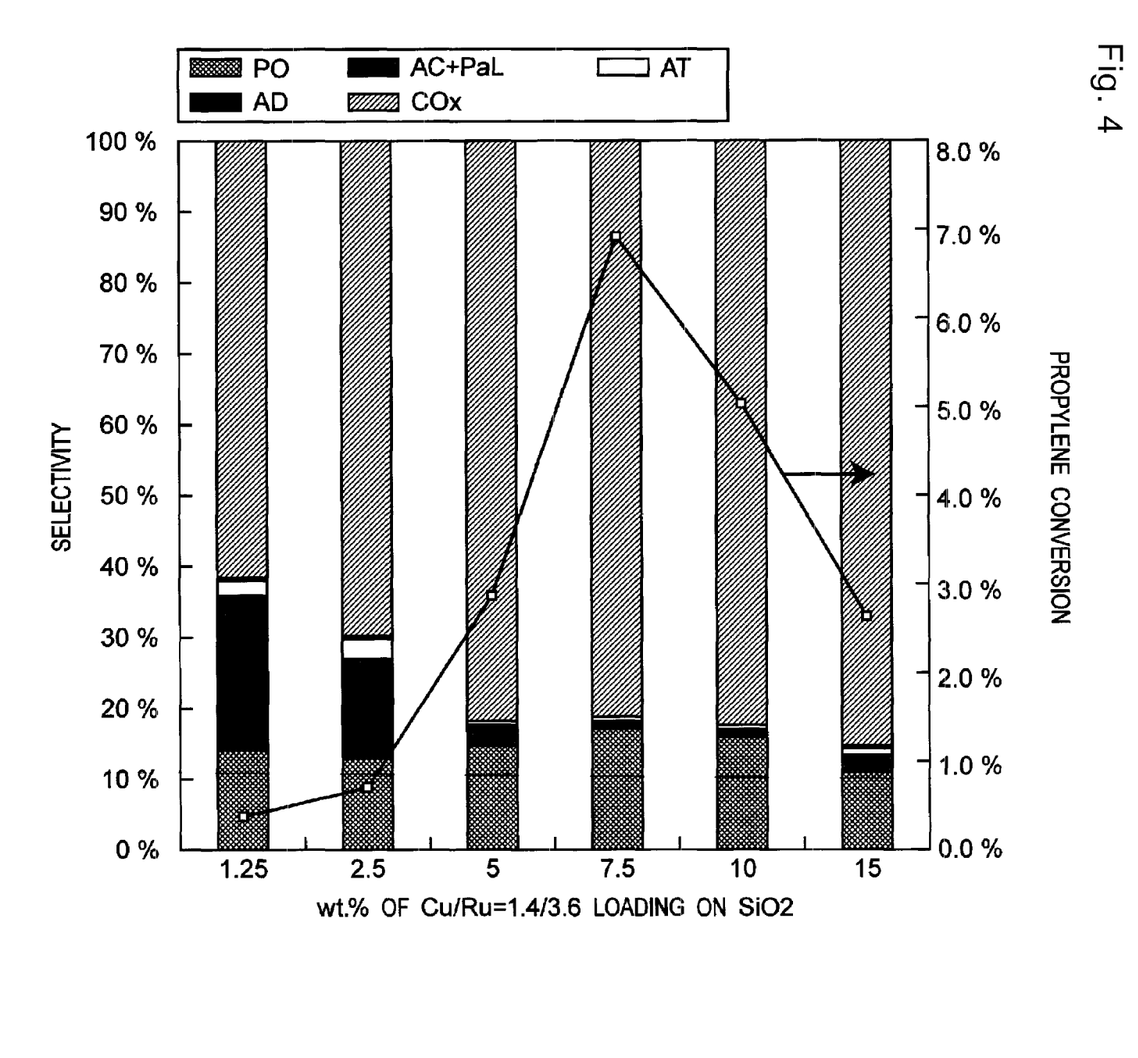
FIG. 4 is a graph showing the result of Example 3, analysis (2).

The results based on the analysis (1) are shown in FIG. 3. The results based on the analysis (2) are shown in FIG. 4.

Example 4

A catalyst was prepared in the same manner as Example 1, except that the metal weight ratio was Ru/Cu=3.6/1.4. Production of propylene oxide was carried out in the same manner as Example 1, except that the catalyst of the present example was used. The mixture gas consisted of 2.5 vol % propylene ($C_3H_6$), 15 vol % $O_2$, and 82.5 vol % He and the reaction temperature was 170, 190, 210, 230, 250, 270, 290 or 310° C.

Figure 5:
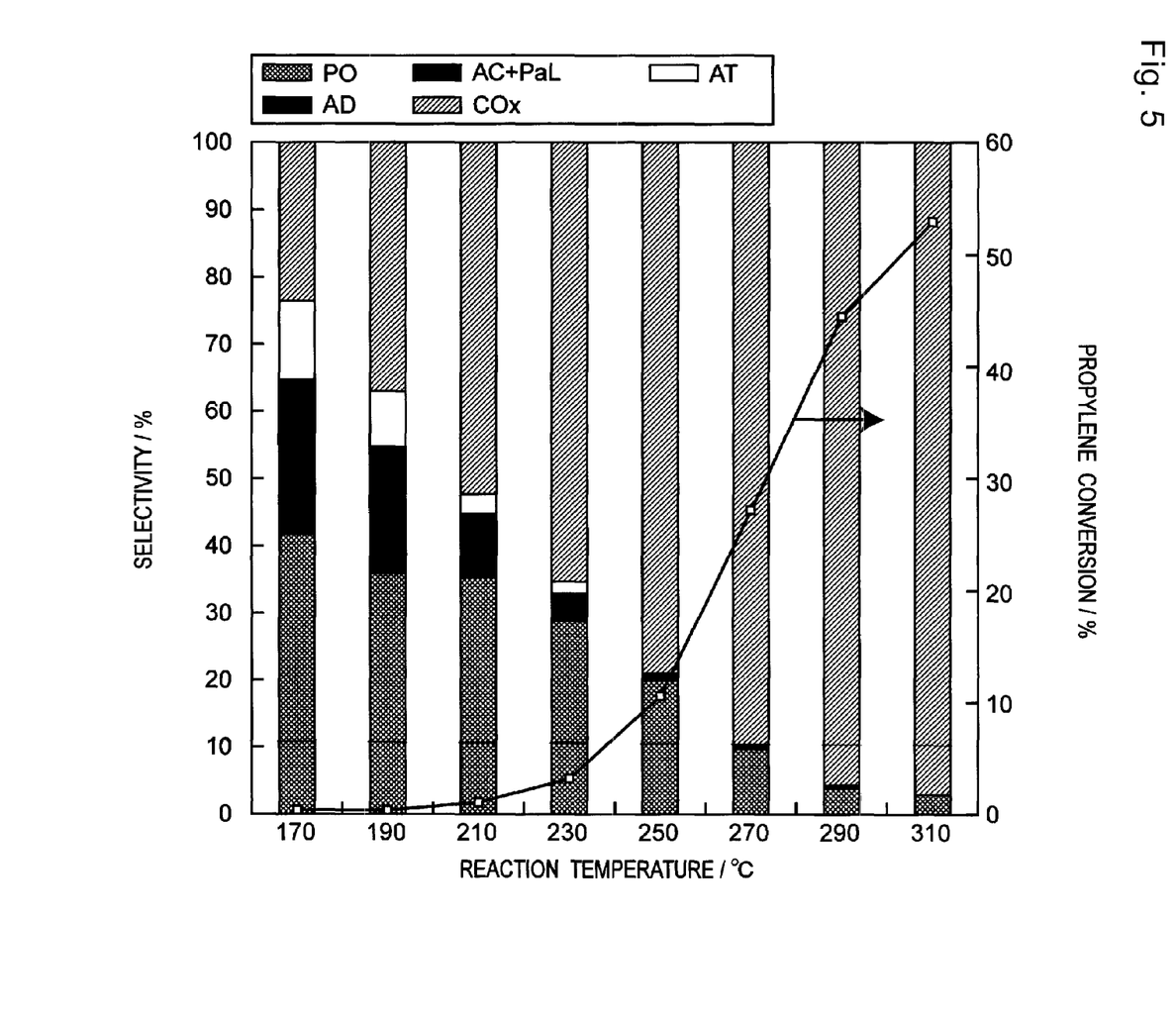
FIG. 5 is a graph showing the result of Example 4, analysis (1).
Figure 6:
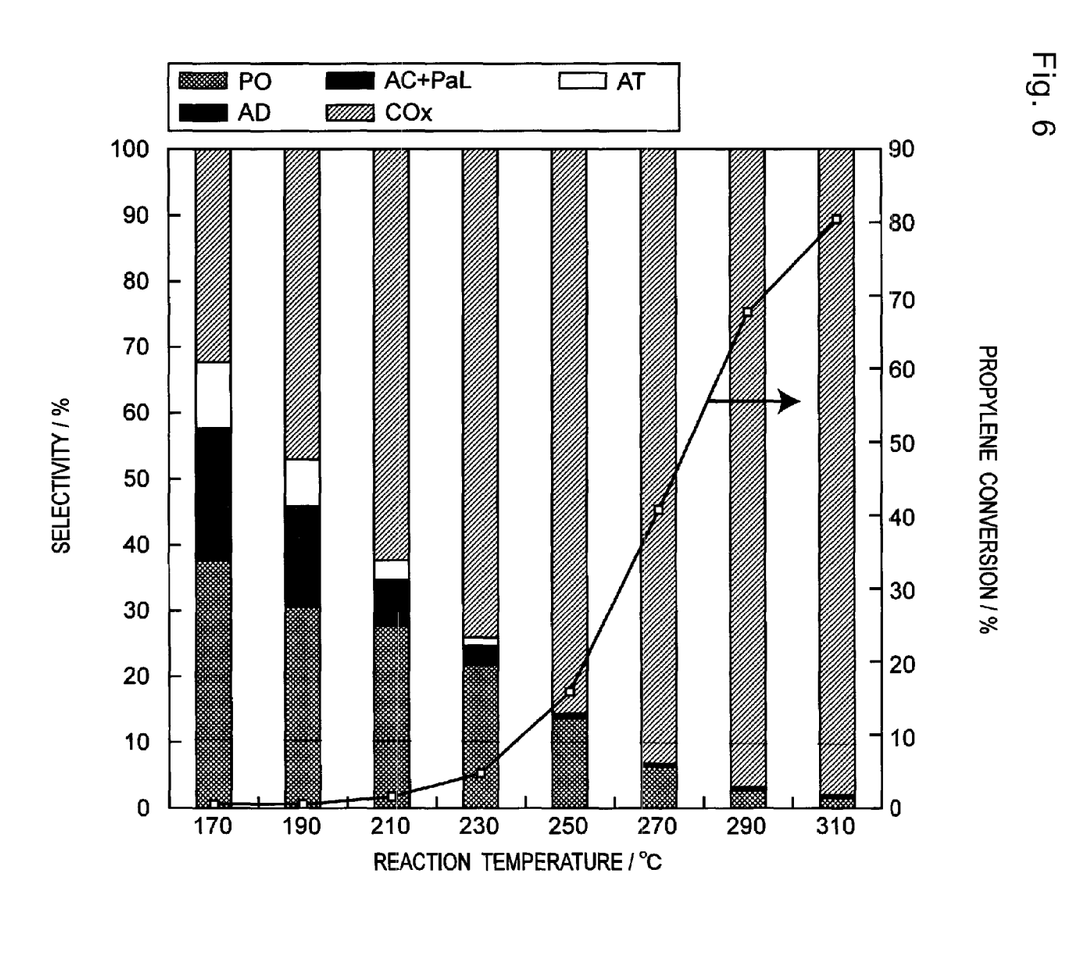
FIG. 6 is a graph showing the result of Example 4, analysis (2).

The results based on the analysis (1) are shown in FIG. 5. The results based on the analysis (2) are shown in FIG. 6.

Example 5

A powder X-ray diffraction (XRD) pattern of the catalyst obtained in Example 1 was determined with PANalytical X'Pert PRO fitted with a Ni filter and a Soller slit collimator. The Cu-$K_\alpha$ radiation at 45 kV and 40 mA was used to identify the active catalyst phases.

The following metal compounds as supported on $SiO_2$ were prepared and examined in the same manner as above: CuO (Cu content, 3.6 wt % of the total of CuO and $SiO_2$)

supported on SiO$_2$ which was prepared from Cu(NO$_3$)$_2$; and RuO$_2$ (Ru content, 7.2 wt % of the total of RuO$_2$ and SiO$_2$) supported on SiO$_2$ which was prepared from (NH$_4$)$_2$RuCl$_6$.

Figure 7:
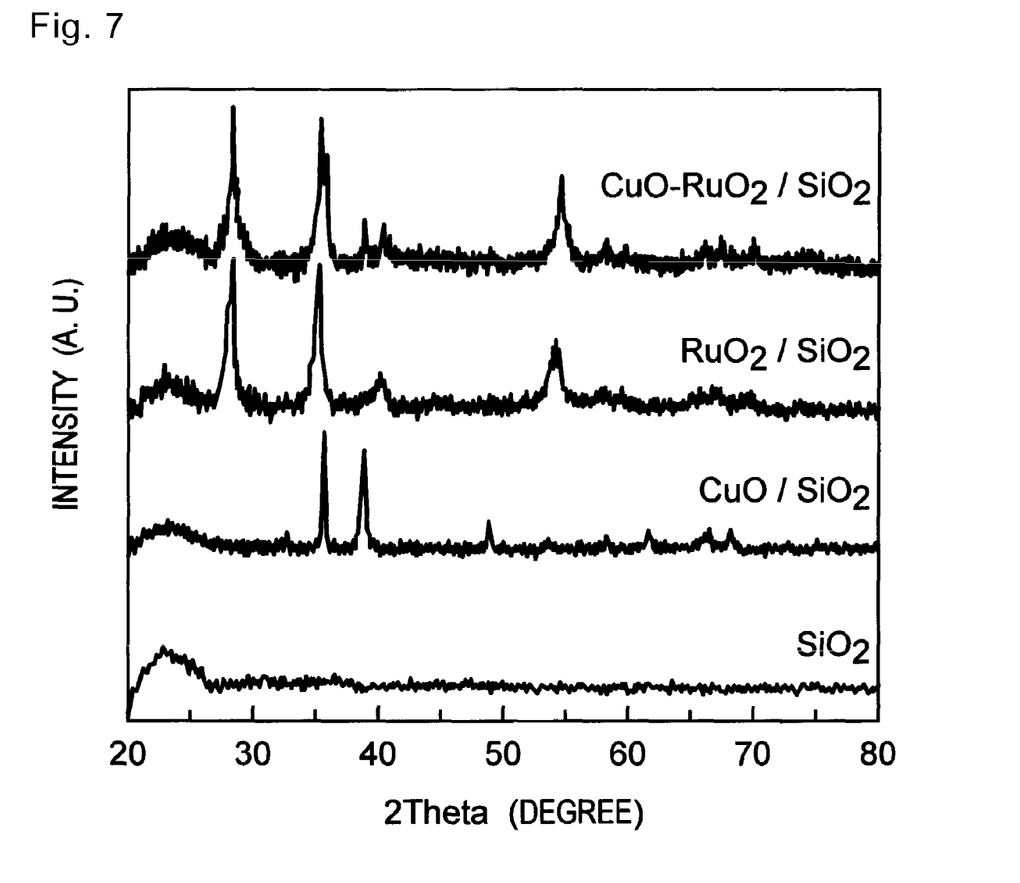
FIG. 7 is a graph showing the powder X-ray diffraction patterns of Example 5.

The XRD patterns are shown in FIG. 7. The XRD pattern of the catalyst shows that it comprises CuO and RuO$_2$ without forming any crystalline mixed metal oxides or alloys.

Example 6

A catalyst is prepared in the same manner as Example 1, except that TiO$_2$ is used instead of SiO$_2$. Production of propylene oxide is carried out in the same manner as Example 1 except that the catalyst is used.

What we claim is:

1. A process for producing an olefin oxide which comprises reacting an olefin with oxygen in the presence of a catalyst comprising a copper oxide and a RuO$_2$ on a porous support, wherein the copper/ruthenium metal weight ratio in the catalyst is 8/92 to 72/28.

2. The process according to claim 1, wherein the porous support comprises Al$_2$O$_3$, SiO$_2$, TiO$_2$ or ZrO$_2$.

3. The process according to claim 1, wherein the porous support comprises SiO$_2$.

4. The process according to claim 1 or 2, wherein the total amount of the copper oxide and the RuO$_2$ in the catalyst is 0.01 to 80% by weight of the amount of the catalyst.

5. The process according to claim 1 or 2, wherein the copper oxide is CuO.

6. The process according to claim 1 or 2, wherein the olefin is propylene and the olefin oxide is propylene oxide.

7. The process according to claim 1 or 2, wherein the catalyst is obtained by impregnating a porous support with a solution containing copper and ruthenium ions to prepare a composition, followed by calcining the composition.

8. The process according to claim 1 or 2, which comprises reacting an olefin with oxygen at a temperature of 100 to 350° C.

9. A catalyst for producing an olefin oxide which comprises a copper oxide and a RuO$_2$ on a porous support.

10. The catalyst according to claim 9 which is obtained by impregnating a porous support with a solution containing copper and ruthenium ions to prepare a composition, followed by calcining the composition.

11. The catalyst according to claim 9 or 10, wherein the porous support comprises Al$_2$O$_3$, SiO$_2$, TiO$_2$ or ZrO$_2$.

12. The catalyst according to claim 9 or 10, wherein the porous support comprises SiO$_2$.

13. The catalyst according to claim 9 or 10, wherein the olefin oxide is propylene oxide.

* * * * *